United States Patent [19]

Earley

[11] 4,195,189
[45] Mar. 25, 1980

[54] PREPARATION OF BIPHENOLS BY THE OXIDATIVE COUPLING OF ALKYLPHENOLS

[75] Inventor: Roger A. Earley, Wilmington, Del.

[73] Assignee: ICI Americas Inc., Wilmington, Del.

[21] Appl. No.: 12,374

[22] Filed: Feb. 15, 1979

[51] Int. Cl.$^2$ .................. C07C 37/00; C07C 39/12
[52] U.S. Cl. .................. 568/730; 260/396 N; 568/644
[58] Field of Search .................. 568/730; 260/396 N

[56] References Cited

U.S. PATENT DOCUMENTS

| | | | |
|---|---|---|---|
| 3,219,625 | 11/1965 | Blanchard et al. | 260/396 N |
| 3,219,626 | 11/1965 | Blanchard et al. | 260/396 N |
| 3,247,262 | 4/1966 | Kaeding | 568/730 |
| 3,306,874 | 2/1967 | Hay | 260/396 N |
| 3,306,875 | 2/1967 | Hay | 568/730 |
| 4,070,383 | 1/1978 | Rutledge | 568/730 |
| 4,096,190 | 6/1978 | Rutledge | 568/730 |
| 4,098,830 | 7/1978 | Rutledge | 568/730 |
| 4,100,202 | 7/1978 | Rutledge | 568/730 |
| 4,100,203 | 7/1978 | Rutledge | 568/730 |
| 4,100,204 | 7/1978 | Rutledge | 568/730 |
| 4,100,205 | 7/1978 | Rutledge | 568/730 |
| 4,100,206 | 7/1978 | Rutledge | 568/730 |
| 4,101,561 | 7/1978 | Rutledge | 568/730 |
| 4,108,908 | 8/1978 | Rutledge | 568/730 |
| 4,132,722 | 1/1979 | Rutledge | 568/730 |
| 4,139,544 | 2/1979 | Rutledge | 568/730 |

OTHER PUBLICATIONS

White et al. I, "J. of Poly Sc.", Part A1, 8:1427–1438 (1970).
White et al. II, "J. of Poly Sc.", Part A1, 10:1565–1578 (1972).
Kaeding, "J. Org. Chem", 28:1063–1067 (1963).

*Primary Examiner*—Norman Morgenstern
*Attorney, Agent, or Firm*—Han Jolyon Lammers

[57] ABSTRACT

2,6-Dialkylphenols may be oxidized in a molten state with an activated basic cupric oxide having a specific surface area to produce carbon-carbon coupled condensation products.

9 Claims, No Drawings

PREPARATION OF BIPHENOLS BY THE OXIDATIVE COUPLING OF ALKYLPHENOLS

BACKGROUND OF THE INVENTION

The present invention concerns a process for preparing a biphenol from an alkylphenol, especially a process for preparing a 3,3',5,5'-tetraalkyl-4,4'-biphenol by the oxidative coupling of a 2,6-dialkylphenol in the presence of a cupric compound.

It is well-known in the art that self-condensation products are obtained when a phenol compound is oxidized. The method employed in preparing diphenoquinones, biphenols or polyphenoxy ethers by oxidizing phenols is generally referred to as the oxidative coupling of phenols.

The self-condensation products resulting from these oxidative coupling reactions can be categorized as either those resulting from the carbon-carbon coupling or carbon-oxygen coupling of said phenols. Biphenols and diphenoquinones are prepared by carbon-carbon coupling in accordance with the following general reaction:

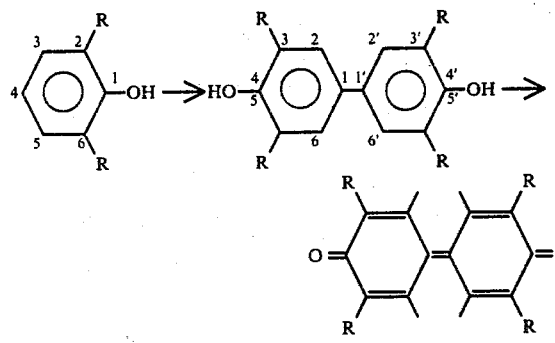

Similarly, polyphenoxy ethers are prepared by carbon-oxygen coupling in accordance with reactions such as the following general reaction:

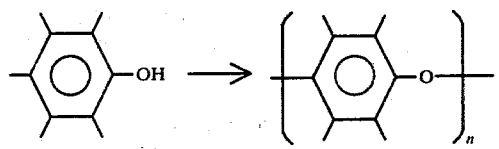

wherein substituents are omitted and n is an integer.

Whether carbon-carbon coupling or carbon-oxygen coupling, occurs depends on the substituents, the oxidizing agents or the catalyst systems employed.

A variety of materials, including metals and various salts, oxides and complexes have previously been disclosed as useful in promoting the oxidative coupling of phenols.

Processes which have been used in the past for the preparation of 3,3',5,5'-tetraalkyl-4,4'-biphenol have generally been two stage processes, involving oxidation of a 2,6-dialkylphenol to a corresponding diphenoquinone, and then reduction by hydrogenation of the diphenoquinone to a corresponding biphenol. The first stage may be carried out in the presence of forced air and optionally with a suitable catalyst or by the use of strong oxidizing agents, such as chromic acid or a ferric salt. Such processes are disclosed for example, in U.S. Pat. Nos. 2,900,417 to A. H. Filbery et al. and 3,491,128 to B. B. Dewhurst.

One stage processes for the preparation of 3,3',5,5'-tetraalkylbiphenol are disclosed by Randell et al. in U.S. Pat. No. 3,812,193 and by Kaeding in U.S. Pat. No. 3,247,262. In Randell et al., 2,6-diisopropylphenol is oxidized to the corresponding biphenol with a ferric salt of a non-oxidizing acid in an aqueous medium. It is also disclosed in Randell et al. that both the ratio of ferric ion to phenol and the ratio of water to phenol are critical and the process is specific to 2,6-diisopropylphenol. In Kaeding, alkylphenols including 2,6-dialkylphenols in molten state are oxidized with a cupric salt of an organic carboxylic acid at about 140° to 225° C. The cupric carboxylate is reduced to the cuprous salt during the reaction and this may be restored to the cupric state by oxidation. It is also disclosed in Kaeding that optimum yields of biphenols are obtained from alkyl phenols which have relatively bulky radicals, for example, isopropyl, tert-butyl, tert-amyl, and where the cupric carboxylate is sufficiently soluble in the molten phenol reaction mixture.

Other one step processes for the preparation of 3,3',5,5'-tetraalkylbiphenol are described by T. F. Rutledge in U.S. Pat. No. 4,070,383, wherein an alkylphenol is oxidized by contacting an aqueous mixture thereof with oxygen in the presence of a catalyst system comprising; (a) a copper compound, (b) an anionic surfactant, and (c) an alkaline material.

A method for oxidizing phenols in liquid form with oxygen in the presence of a small amount of catalyst, such as precipitated cupric oxide, is disclosed in German Pat. No. 536,277.

The present invention possesses one or more advantages over the prior art which may be summarized as follows.

1. A polluting discharge of aqueous effluent may be avoided.
2. Organic solvents are avoided during the oxidation stage.
3. The spent oxidizing agent may be readily separated and recycled for further use.

SUMMARY OF THE INVENTION

In accordance with the present invention, a carbon-carbon coupled condensation product is prepared by contacting a 2,6-dialkylphenol in a molten state with an oxidizing agent consisting essentially of activated basic cupric oxide having a surface area of from 5 to about 50 m2/gram.

DESCRIPTION OF THE PREFERRED EMBODIMENTS

2,6-Dialkylphenol

Any 2,6-dialkylphenols which have alkyl groups of 1 to 6 carbon atoms may be employed. These alkyl groups include primary, secondary and tertiary alkyl groups. Examples of primary alkyl groups are; methyl, ethyl, n-propyl, n-butyl, iso-butyl, n-amyl and n-hexyl. Examples of secondary alkyls are; iso-propyl and sec-butyl. An example of tertiary alkyl group is tert-butyl.

The process of the present invention is exceedingly suitable for the oxidation of 2,6-dialkylphenols having primary alkyl groups, although it is also applicable to the oxidation of 2,6-dialkylphenols having secondary or tertiary alkyl groups.

2,6-Dialkylphenols having different alkyl groups in a molecule may be employed as well as those having the same alkyl groups in a molecule. 2,6-Dialkylphenols having the same alkyl groups in a molecule, such as 2,6-dimethylphenol (2,6-xylenol), 2,6-diisopropylphenol, 2,6-di-t-butylphenol are suitable starting materials in the instant process.

While the purity of 2,6-dialkylphenol used in accordance with the present invention is not critical, a purity of more than 90% and preferably about 99% obviates additional purification of the biphenol.

Cupric Compound

The activated basic cupric oxide which is employed in the process of the present invention should have the following properties:
(a) a surface area about 5 to about 50 m$^2$/gram, and
(b) sufficient basicity to allow 4.0 grams of the activated cupric oxide in 100 ml of deionized water, to indicate a pH of about 7 to about 10.

The basic property of the activated cupric oxide which is described as the ability to achieve a pH of 7 to 10 when the activated cupric oxide is placed in deionized water in a ratio of 4 to 100 (which is referred to as apparent pH in this specification), is critical to the present invention. An apparent pH lower than about 7 retards the oxidation reaction, and an apparent pH higher than about 10 results in the formation of undesirable amounts of by-product. An apparent pH range from about 8 to about 9 is preferred. Best results are obtained at an apparent pH about 8.

The surface area of the activated cuprix oxide is also an important characteristic of the oxidation agent.

A surface area of about 5 to about 50 m$^2$/gram is suggested, with about 20 to 30 m$^2$/gram as the preferred range.

A preferred method of preparing activated cuprix oxide having the properties described above is heating cupric hydroxide precipitated from water soluble cupric compound solution under such conditions that the slightly basic property of the cupric oxide is maintained. A typical procedure is as follows:

A water soluble cupric salt, such as cupric nitrate, cupric sulfate, cupric chloride or cupric acetate is dissolved in water. An alkali is added to the solution to form a basic solution, from which cupric hydroxide precipitates. Sodium hydroxide or potassium hydroxide is the preferred alkali. Suitable amounts of alkali may be added until pH of the solution reaches strongly alkaline, that is, pH about 14. Then the solution is heated to about 50° to 100° C., whereby the cupric hydroxide is converted into cupric oxide. The cupric oxide is filtered and washed with water and may be washed again with a diluted alkaline solution in order to maintain the slightly basic characteristics of the cupric oxide. Sodium hydroxide or potassium hydroxide is a preferred alkali. The cupric oxide then is dried by heating, preferably at about 150° to about 350° C., and then ground to a powder for use in the oxidative coupling reaction.

The activated cupric oxide prepared by this procedure has the properties prescribed above. The apparent pH of the activated cuprix oxide may be controlled by the amount and the concentration of the alkaline wash solution and the amount of wash water. Methods for measuring the apparent pH and the surface area are well-known in the art.

Spent oxidation agent from the process of the invention may be recycled. For example, the mixture of cuprous oxide and cupric oxide which remains in the residue after most of the organic compounds are leached from the reaction mass with a polar organic solvent and a chlorinated hydrocarbon solvent may be converted to activated cupric oxide. Regenerated activated cupric oxide may be obtained by heating the mixture of cuprous oxide and cupric oxide in the presence of oxygen and oxygen containing gas at 150° to 350° C., preferably in air at about 300° C.

Reaction Conditions

Preferably the 2,6-dialkylphenol is oxidized with activated cupric oxide in a dry non-solvent molten state, at a temperature between the melting point and the boiling point of 2,6-dialkylphenol, with a molar ratio of activated cupric oxide to 2,6-dialkylphenol of 1.0 to 1.8 until substantial amounts of biphenol are obtained.

While the molar ratio of activated cupric oxide to 2,6-dialkylphenol is not extremely critical, molar ratios of about 1.0 to about 1.8 are preferred for best results. Molar ratios of about 1.0 to about 1.5 are preferred when activated cupric oxide prepared by heating cupric hydroxide is employed, and molar ratios of about 1.0 to about 1.6 are preferred when activated cupric oxide regenerated by the heating of a mixture of cuprous oxide and cupric oxide is employed, as some surface areas may be lost during recycling.

The oxidative coupling reaction may be carried out at a temperature between the melting point and the boiling point of 2,6-dialkylphenol. Preferred reaction temperatures are 95° to 200° C. and optimum temperatures range from about 100° to 150° C. Temperatures lower than 95° C. result in a lower conversion rate, and temperatures higher than 200° C. result in the formation of undesirable by-product. Reaction temperatures at about 100° C. are most convenient because the temperature can be easily controlled using steam.

Reaction times generally depend on the reaction temperature. Lower temperatures need longer reaction times, higher temperatures require shorter reaction times. Short reaction times at high temperatures frequently result in more by-product formation. Constant high yields of the biphenol may be obtained by a reaction at about 100° C. for about 1.5 to 4.0 hours. The oxidative coupling reaction may be terminated easily by lowering the temperature, for example by cooling with running water.

It is important in accordance with the present invention that the oxidative coupling reaction is carried out under such conditions that the molten 2,6-dialkylphenol is sufficiently contacted with the activated cupric oxide in a uniform phase. The presence of water, methanol or pyridine, substantially reduces the yield of the biphenol. Some type of agitation should be supplied to ensure that no segregation of materials occurs. Suitable agitation means are well-known in the art.

The oxidative coupling reaction may be carried out in air or in an inert atmosphere. Any type of container may be used, a closed one is preferred in order to prevent the escape of 2,6-dialkylphenols.

Recovery of Biphenol

The reaction mass generally consists of organic compounds including unreacted 2,6-dialkylphenol, biphenol, small amounts of diphenoquinone, and other organic impurities, and a copper oxide mixture of cuprous oxide and cupric oxide.

The biphenol may be recovered from the reaction mass by leaching it with an organic solvent or by leaching it with an aqueous alkaline solution.

Any polar organic solvent that; (1) exhibits a high solubility for the biphenol, unreacted 2,6-dialkylphenol, diphenoquinone and the other organic impurities, (2) is chemically inert in respect to the copper oxide and the phenols and (3) is easy to separate from the solution containing biphenol, unreacted 2,6-dialkylphenol diphenoquinone and other organic impurities, may be employed. These polar organic solvents include lower alcohols, such as methanol, ethanol and isopropanol; low molecular weight ketones, such as acetone and methyl ethyl ketone; lower molecular weight esters, such as methyl acetate, ethyl acetate; and lower molecular weight ethers, such as diethyl ether, dioxane, and tetrahydrofuran. Acetone is the most convenient solvent because it dissolves most organic compounds and is inexpensive. The organic solvent may be added to the reaction mass in a sufficient amount to dissolve most organic compounds. More than about twice the theoretical amount of organic solvent based on the solubility of the biphenol can usually dissolve most organic compounds.

A chlorinated hydrocarbon solvent is preferably added to the reaction mass in addition to the polar organic solvent to dissolve diphenoquinone which is the most difficult organic compound to remove. These chlorinated hydrocarbon solvents include methylene chloride, dichloroethane, chloroform and chlorobenzene. Methylene chloride, which is inexpensive and easily available, is the preferred chlorinated hydrocarbon solvent. A small amount of a chlorinated hydrocarbon solvent may be added to the reaction mass either in a mixture with the polar organic solvent or as a secondary wash after treatment with the polar organic solvent.

In general the reaction mass is slurried with the organic solvent, after which the copper oxide mixture is separated from the organic liquid layer by filtration. The copper oxide mixture may then be recycled. The organic solvent is separated from the organic compounds by a suitable method, such as vacuum distillation and may also be recycled.

The biphenol may also be recovered from the reaction mass by leaching the reaction mass with an aqueous alkaline solution. Any strong alkali may be employed to dissolve phenol compounds including unreacted 2,6-dialkylphenol and the biphenol from the reaction mass into the aqueous alkaline solution. These strong alkali include, for example, sodium hydroxide and potassium hydroxide. The phenol compounds are dissolved in the aqueous alkaline solution forming water soluble salts, then the aqueous solution may be separated from copper oxide mixture by filtration. On adding sufficient amounts of a strong acid such as hydrochloric the or sulfuric acid to the filtered aqueous solution, the phenol compounds will precipitate from the aqueous solution. The precipitates may be collected by a suitable method, for example, filtration.

Leaching with a polar organic solvent is preferred to leaching with an aqueous alkaline solution, because; (1) the polluting discharge of aqueous effluent may be avoided, (2) a polar organic solvent may be recycled after being separated from the reaction product, (3) the copper oxide mixture can easily be removed and recycled for further use, (4) further oxidation which occurs when the biphenol is in the presence of an aqueous alkaline solution may be avoided. Leaching with a chlorinated hydrocarbon solvent in addition to a polar organic solvent either in a mixture with the polar organic solvent or as a secondary wash after treatment with the polar organic solvent is especially preferred, because a copper oxide mixture can be recycled without any further treatment except regeneration.

The biphenol recovered from the reaction mass, which is the desired carbon-carbon coupled product 3,3',5,5'-tetraalkyl-4,4'-biphenol may be used without further treatments, or may be further purified, if desired. While any useful method for the purification of the biphenol may be employed, for example, by recrystallization, washing with hot water or washing with a solvent purification by sublimation is the preferred method because a purer product is obtained by this method than by any known other procedure.

Recycling of Copper Oxide

The copper oxide mixture of cuprous oxide and cupric oxide present in the reaction mass may be recycled by leaching the biphenol with a polar organic solvent and regenerating the copper oxide mixture. This mixture is preferably recycled by leaching with a chlorinated hydrocarbon solvent in addition to a polar organic solvent. The leached oxide mixture containing the cuprous oxide portion may be oxidized to cupric oxide and activated cupric oxide and regenerated by heating it in the presence of oxygen, for example, in air, at about 300° C.

Unexpectedly, it was found that the copper oxide did not substantially deteriorate after it was recycled three times by leaching the biphenol from the reaction mass with a polar organic solvent/chlorinated hydrocarbon solvent and subsequent regeneration in air at 300° C. The oxidizing agent's performance may be maintained if the copper oxide is recycled by leaching the reaction mass with a polar organic solvent and a chlorinated hydrocarbon solvent, and regenerating the copper oxide in air at 300° C. provided small amounts of fresh activated cupric oxide are added each time primarily to compensate for physical loss. A preferred chlorinated hydrocarbon solvent is methylene chloride.

Biphenols prepared in accordance with the present invention are suitable for any use heretofore described in the art. For example, the biphenols may be employed as stabilizers in gasoline and other petroleum products such as described in U.S. Pat. No. 2,479,948 or the biphenols may be considered as intermediate reaction products which may be further reacted to form polycarbonates, polyesters or epoxies.

In order to describe the present invention so it may be understood more clearly, the following examples are set forth. All parts in examples are based on weight unless otherwise indicated. Surface area of the cupric oxide is measured using "Automatic Surface Area Analyzer, Model 2200" manufactured by Micrometrities Instrument Corporation. All apparent pH's are determined by placing 4.0 grams of cupric oxide in 100 grams of deionized water.

EXAMPLE 1

Preparation of Activated Cupric Oxide 211.2 grams of cupric nitrate ($Cu(NO_3)_2.3H_2O$) is dissolved in enough water to form a clear solution. To the solution enough 10 N sodium hydroxide solution is added until a pH of 14 is indicated. The solution is heated to near boiling while being gently stirred. The solution is maintained under heat until all signs of blue color are absent. The slurry is filtered using a Buchner Funnel. The cake is then washed with four liters of solution prepared by adding 1.6 ml of 10 N sodium hydroxide to four liters of water. The cake is sucked dry and placed in an oven heated at 300° C. overnight to dry. The dry cake is ground to fine powder using a mortar and pestle. The surface area of the activated cupric oxide is 26.4 m2/grams. 4 grams of the activated cupric oxide is put into 100 ml of deionized water. pH of the aqueous layer is 7.75.

Reaction of 2,6-dimethylphenol (with activated cupric oxide)

4.509 grams of cupric oxide (56.6 m mol) which is prepared above, is mixed with 5.004 grams of 2,6-dimethylphenol (2,6-xylenol, 41.0 m mol). The mixture is placed in a closed container equipped with magnetic stirring bar. The container is submerged in a beaker of water which is heated to 100° C. on top of a hot plate. After being left in the water for three hours, the container is removed and cooled with running water.

1.014 grams of the reaction mass is taken and leached with 250 ml of acetone. The gas liquid chromatography analysis shows that the product contains 93.5% of 3,3',5,5'-tetramethyl biphenol (TMBP) and 3.6% of unreacted 2,6-dimethylphenol.

EXAMPLE 2

2,6-xylenol is mixed with activated cupric oxide prepared by the similar procedure of Example 1 in weight amounts in the following table. The mixture is placed in a closed container equipped with magnetic stirring bar. The container is submerged in a beaker of water which is heated to 100° C. on top of a hot plate. After being left in water for a suitable length of time, the container is removed and cooled with running water.

The reaction mass is leached with acetone until a clear solution is obtained and then with a small amount of methylene chloride. The product is analyzed by gas liquid chromatography.

Results are shown in the following table:

| | | Reactant | | | | |
|---|---|---|---|---|---|---|
| React. Time (hr.) | Activ. Weight (g) | Cupric Oxide Surface Area (m$^2$/g) | Apparent pH | 2,6-Xylenol Weight (g) | Molar Ratio* | Yield of TMBP (%) |
| 2.5 | 6.51 | 22.1 | 7.00 | 7.21 | 1.38 | 62 |
| 3.0 | 6.51 | 40.1 | 8.68 | 7.25 | 1.38 | 95 |
| 3.0 | 6.51 | 13.0 | 9.24 | 7.24 | 1.38 | 88 |
| 3.0 | 4.06 | 28.2 | 9.70 | 5.03 | 1.24 | 88 |
| 3.0 | 4.01 | 25.7 | 10.10 | 5.02 | 1.23 | 63 |

*Molar Ratio (activated cupric oxide/2,6-xylenol).

EXAMPLE 3

Recycling of Copper Oxide

A mixture of cuprous oxide and cupric oxide is recovered from a reaction mass by leaching with acetone until a clear solution is obtained and then with a small amount of methylene chloride. The copper oxide mixture is heated in air at 300° C. overnight. 2,6-Xylenol (amount employed thereof is shown in the following table) is mixed with thus regenerated activated cupric oxide (amount employed thereof is shown in the table). The mixture of 2,6-xylenol and activated cupric oxide is placed in a closed container equipped with a magnetic stirring bar. The container is submerged in a beaker of water, which is heated to 100° C. on top of a hot plate. After being left in the water for three hours, the container is removed and cooled with running water. The reaction mass is leached with acetone until a clear solution is obtained and then with a small amount of methylene chloride. The product is analyzed with gas liquid chromatography. Mixture of cuprous oxide and cupric oxide is collected.

This product is used in the process three times with a recycling after each use and fresh activated cupric oxide. Results are shown in the following table:

| | Reactant | | | Product | |
|---|---|---|---|---|---|
| Times Recycled | Recycled Activated Cupric Oxide (gm) | 2,6-Xylenol (gm) | Molar* Ratio | Unreacted 2,6-Xylenol (%) | TMBP (%) |
| 1 | 4.512 | 5.092 | 1.358 | 3.0 | 84 |
| 2 | 4.332 | 4.366 | 1.521 | 4.6 | 90 |
| 3 | 3.989 | 4.003 | 1.528 | 6.4 | 89 |

*Molar Ratio (activated cupric oxide/2,6-xylenol).

EXAMPLE 4

Recycling of Copper Oxide

Copper oxide, which is a mixture of cuprous oxide and cupric oxide is recovered from a reaction mass by leaching with acetone until a clear solution is obtained and then with a small amount of methylene chloride. The copper oxide mixture is heated in air at 300° C. overnight. Fresh activated cupric oxide prepared in Example 1, (amount employed thereof is shown in the following table) is combined with thus regenerated activated cupric oxide (amount employed thereof is also shown in the following table). The combined activated cupric oxide is mixed with 2,6-xylenol (amount employed thereof is shown in the following table). The mixture is placed in a closed container equipped with a magnetic stirring bar. The container is submerged in a beaker of water, which is heated to 100° C. on top of a hot plate. After being left in the water for three hours, the container is removed and cooled with running water. The reaction mass is leached with acetone until a clear solution is obtained and then with a small amount of methylene chloride. The product is analyzed by gas liquid chromatography. Mixture of cuprous oxide and cupric oxide is collected.

The results of the efficacy of the recycled product are shown in the following table:

| | Reactant | | | | Product | |
|---|---|---|---|---|---|---|
| Times Recycled | Recycled Activated Cupric Oxide (gm) | Fresh Activated Cupric Oxide (gm) | 2,6-Xylenol (gm) | Molar* Rate | Unreacted 2,6-Xylenol (%) | TMBP (%) |
| 1 | 4.429 | 0.600 | 5.060 | 1.523 | 4.9 | 93 |
| 2 | 4.503 | 0.503 | 5.050 | 1.520 | 15.0 | 69 |
| 3 | 4.498 | 0.510 | 5.043 | 1.522 | 13.4 | 86 |
| 4 | 4.506 | 0.515 | 5.072 | 1.518 | 9.0 | 85 |
| 5 | 4.518 | 0.529 | 5.093 | 1.519 | 7.2 | 91 |
| 6 | 4.512 | 0.516 | 5.100 | 1.511 | 5.2 | 93 |
| 7 | 4.507 | 0.513 | 5.071 | 1.518 | 4.6 | 94 |

*Molar ratio (combined activated cupric oxide/2,6-xylenol)

EXAMPLE 5

Activated cupric oxide prepared in Example 1, is mixed with 2,6-xylenol. The mixture is placed in a closed container equipped with a magnetic stirring bar. The container is submerged in a beaker of water or oil (temperature of which is fixed to reaction temperature shown in the following table), the container is removed and cooled with running water. The reaction mass is leached with 10 N sodium hydroxide solution. The aqueous solution is separated by filtration. The copper oxide cake is washed with water and a diluted sodium hydroxide solution. Both aqueous solutions are combined. The aqueous solution is acidified with hydrochloric acid solution until pH reached to about 2. The resulting precipitate is collected by filtration, then washed with water. The product is analyzed by gas liquid chromatography. Results are shown in the following table:

| Reaction Temp. °C. | Reaction Time (hr) | Reactant Activated Cupric Oxide (gm) | 2,6-Xylenol (gm) | Molar* Ratio | Yield of TMBP (%) |
|---|---|---|---|---|---|
| 80 | 3.0 | 4.028 | 5.019 | 1.230 | 8 |
| 88 | 3.0 | 4.013 | 5.019 | 1.226 | 23 |
| 95 | 3.0 | 4.017 | 5.022 | 1.226 | 68 |
| 100 | 3.0 | 4.019 | 5.018 | 1.228 | 95 |
| 100 | 3.0 | 3.271 | 5.040 | 0.995 | 97 |
| 150 | 3.0 | 0.650 | 0.990 | 0.998 | 97 |
| 160 | 2.0 | 0.661 | 1.014 | 0.999 | 78 |
| 170 | 2.0 | 0.644 | 1.004 | 0.983 | 95 |
| 180 | 2.0 | 0.649 | 1.010 | 0.985 | 75 |
| 190 | 1.5 | 0.642 | 1.016 | 0.969 | 90 |
| 225 | 2.0 | 0.823 | 1.004 | 1.258 | 54 |

*Molar ratio (activated cupric oxide/2,6-xylenol)

What is claimed is:

1. A process for preparing carbon-carbon coupled condensation products from a 2,6-dialkylphenol which comprises contacting the 2,6-dialkylphenol in a molten state with an oxidizing agent consisting essentially of activated basic cupric oxide having a surface area of from 5 to about 50 m$^2$/gram.

2. A process according to claim 1, wherein said 2,6-dialkylphenol is oxidized at 95° too 200° C. with said oxidizing agent.

3. A process according to claim 1, wherein said 2,6-dialkylphenol is a 2,6 primary alkylphenol.

4. A process according to claim 3, wherein the condensation product is 3,3',5,5'-tetramethyl-4,4'-biphenol and is subsequently recovered by the leaching with a polar organic solvent.

5. A process according to claim 4, wherein;
(A) 2,6-dimethylphenol is oxidized with said activated cupric oxide at 95° to 200° C. to yield 3,3',5,5'-tetramethyl-4,4'-biphenol and wherein the molar ratio of the activated cupric oxide to 2,6-dimethyl-phenol being 1.0 to 1.8 and
(B) the 3,3',5,5'-tetramethyl-4,4'-biphenol is recovered from the reaction mass by the leaching with a polar organic solvent and a chlorinated hydrocarbon solvent.

6. A process according to claim 5, wherein the oxidizing agent is recycled by recovering it and regenerated it by heating it in air at about 300° C.

7. A process according to claim 5, wherein said polar organic solvent is acetone.

8. A process according to claim 5, wherein said chlorinated hydrocarbon solvent is methylene chloride.

9. A process according to claim 5, wherein the oxidizing agent contains recycled copper oxide.

* * * * *

UNITED STATES PATENT AND TRADEMARK OFFICE
CERTIFICATE OF CORRECTION

PATENT NO. : 4,195,189
DATED : March 25, 1980
INVENTOR(S) : Roger A. Earley

It is certified that error appears in the above-identified patent and that said Letters Patent are hereby corrected as shown below:

Column 3, lines 37 and 62, "activated cuprix" should read --activated cupric--.

Column 8, line 61, "4.429" should read --4.428--.

Signed and Sealed this

Fifteenth Day of July 1980

[SEAL]

Attest:

SIDNEY A. DIAMOND

Attesting Officer

Commissioner of Patents and Trademarks